(12) United States Patent
Hedvati et al.

(10) Patent No.: US 7,563,814 B2
(45) Date of Patent: Jul. 21, 2009

(54) OLMESARTAN MEDOXOMIL WITH REDUCED LEVELS OF IMPURITIES

(75) Inventors: Lilach Hedvati, Doar Na Hefer (IL); Gideon Pilarsky, Holon (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 340 days.

(21) Appl. No.: 11/217,473

(22) Filed: Sep. 2, 2005

(65) Prior Publication Data
US 2006/0149078 A1 Jul. 6, 2006

Related U.S. Application Data

(60) Provisional application No. 60/640,232, filed on Jan. 3, 2005.

(51) Int. Cl.
*A61K 31/40* (2006.01)
*C07D 233/00* (2006.01)

(52) U.S. Cl. ...................... 514/385; 548/250

(58) Field of Classification Search ................. 514/385; 548/300.1
See application file for complete search history.

(56) References Cited

U.S. PATENT DOCUMENTS

| 5,616,599 | A | * | 4/1997 | Yanagisawa et al. ........ 514/381 |
| 5,621,134 | A | | 4/1997 | Katsura et al. |
| 6,040,454 | A | | 3/2000 | Koguro et al. |
| 6,111,114 | A | | 8/2000 | Salibeni et al. |
| 6,214,999 | B1 | | 4/2001 | Biard et al. |

FOREIGN PATENT DOCUMENTS

| DE | 197 57 995 | 7/1999 |
| EP | 0 838 458 | 4/1998 |
| EP | 1 555 260 | 7/2005 |
| JP | 6-298683 | 10/1994 |
| JP | 7-053489 | 2/1995 |
| JP | 11-292851 | 10/1999 |
| JP | 11-302260 | 11/1999 |
| WO | WO 95/32962 | 12/1995 |

OTHER PUBLICATIONS

H. Koike et al. "Olmesartan Medoxomil, A Novel Potent Angiotensin II Blocker", *Annu. Rep. Sankyo Res. Lab*, 55, pp. 1-91, (2003).
Larsen et al., "Efficient Synthesis of Losartan, A Nonpeptide Angiotensin II Receptor Antagonist" *Journal Of Organic Chemistry*, vol. 59, No. 21, 6391-6394, (1994).
Attanasi et al., "Synthesis of Biphenylyltetrazole Derivatives of 1-Aminopyrroles as Angiotensin II Antagonists", *II Farmaco*, vol. 54, pp. 64-76, (1999).

* cited by examiner

*Primary Examiner*—Golam M. M. Shameem
*Assistant Examiner*—Susannah Chung
(74) *Attorney, Agent, or Firm*—Kenyon & Kenyon LLP

(57) ABSTRACT

The present invention provides the preparation of olmesartan medoxomil containing less than about 0.1% of one or more of the impurities OLM-Me, OLM-Cl, and OLM-eliminate.

14 Claims, 1 Drawing Sheet

OLMESARTAN MEDOXOMIL WITH REDUCED LEVELS OF IMPURITIES

This application claims the benefit of U.S. Provisional Patent Application Ser. No. 60/640,232 filed Jan. 3, 2005.

FIELD OF INVENTION

The present invention relates to olmesartan medoxomil with reduced levels of impurities.

BACKGROUND OF THE INVENTION

The chemical name for olmesartan medoxomil is 4-(1-hydroxy-1-methylethyl)-2-propyl-1-[[2'-(1H-tetrazol-5-yl)[1,1'-biphenyl]-4-yl]methyl]-1H-imidazole-5-carboxylic acid (5-methyl-2-oxo-1,3-dioxol-4-yl)methyl ester (Merck Index 13th ed.).

The chemical structure of olmesartan medoxomil is:

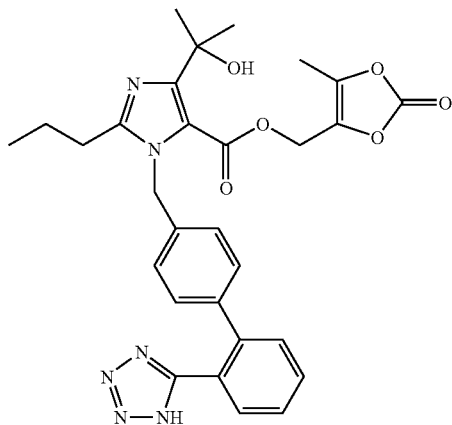

The empirical formula is $C_{29}H_{30}N_6O_6$.
The molecular weight is 558.58.

Olmesartan medoxomil is a prodrug that is hydrolyzed during absorption, and it is a selective $AT_1$ subtype angiotensin II receptor antagonist. Olmesartan medoxomil is disclosed by U.S. Pat. No. 5,616,599 to Yanagisawa et al. It is marketed as BENICAR® in film-coated tablets of 5 mg, 20 mg, and 40 mg for treatment of hypertension in a human.

The synthesis of olmesartan medoxomil (OLM-Mod) per se is illustrated as follows (see also Annu. Rep. Sankyo Res. Lab 2003, 55, 1-91):

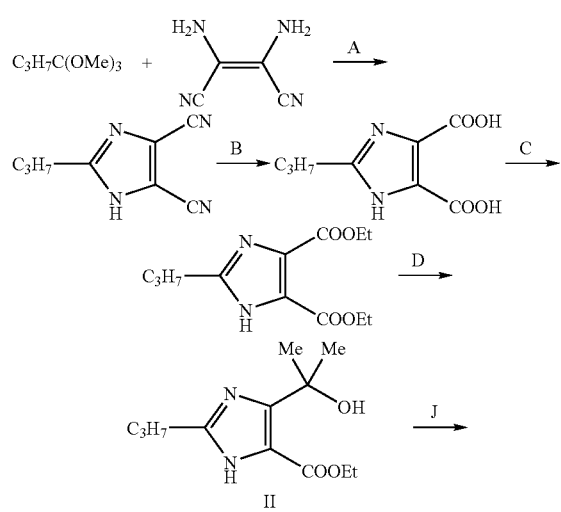

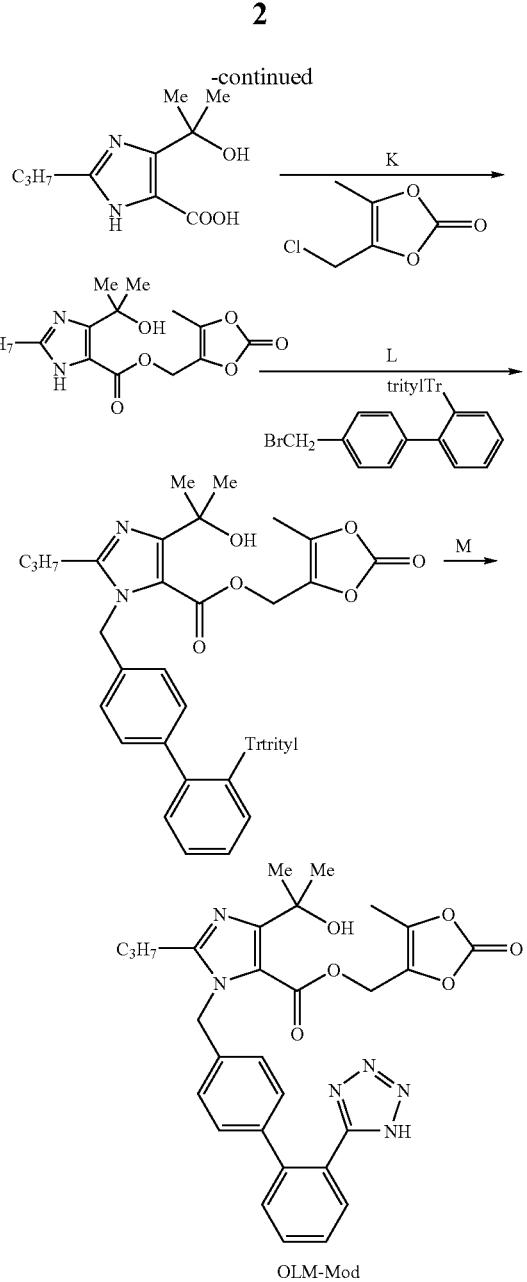

OLM-Mod

But this route of synthesis produces several impurities.
There is a need for processes for preparing olmesartan medoxomil with reduced levels of impurities.

SUMMARY OF THE INVENTION

Figure 1:
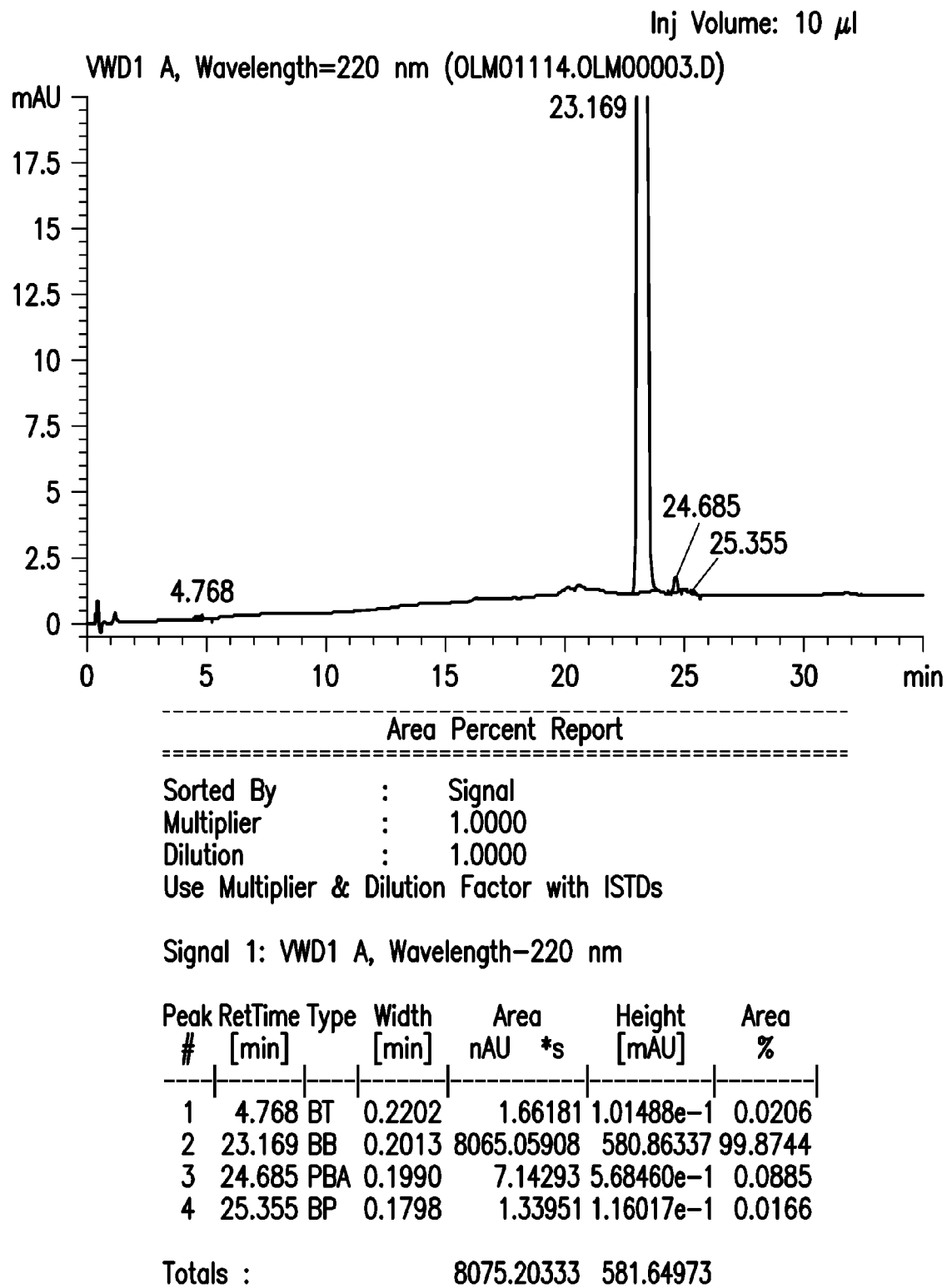
FIG. 1 depicts a typical chromatogram of a trityl olmesartan medoxomil (MTT) sample.

In one aspect, the present invention provides a process for preparing olmesartan medoxomil containing less than about 0.1% area by HPLC of one or more of the following impurities: OLM-Me, OLM-Cl, and OLM-eliminate. This process includes the steps of: obtaining a sample of trityl olmesartan medoxomil (MTT); measuring the amount of one or more impurities selected from the group consisting of MTT-Me, MTT-Cl, and MTT-eliminate in the sample of trityl olmesartan medoxomil; selecting a sample of trityl olmesartan medoxomil in which the amount of one or more of the measured impurities is less than about 0.1%; and synthesizing olmesartan medoxomil from the selected trityl olmesartan medoxomil sample. Preferably, the amount of each of the three impurities in the starting material and/or the final product is less than about 0.1%. More preferably, the combined amount of the three impurities is less than about 0.1%.

DETAILED DESCRIPTION OF THE INVENTION

The present invention provides a process for preparing olmesartan medoxomil containing less than about 0.1% area by HPLC of one or more of the impurities OLM-Me, OLM-Cl and OLM-eliminate.

Impurity OLM-Me is 4-(1-methoxy-1-methylethyl)-2-propyl-1-[2'-(1H-tetrazole-5-yl)biphenyl-4-ylmethyl]imidazole-5-carboxylic acid 5-methyl-2-oxo-1,3-dioxol-4-ylmethyl ester.

Impurity OLM-Cl is 4-(1-hydroxy-1-methylethyl)-2-propyl-1-[2'-(1H-tetrazole-5-yl)biphenyl-4-ylmethyl]imidazole-5-carboxylic acid 5-chloromethyl-2-oxo-1,3-dioxol-4-ylmethyl ester.

Impurity OLM-eliminate is 4-(1-methylethylene)-2-propyl-1-[2'-(1H-tetrazole-5-yl)biphenyl-4-ylmethyl]imidazole-5-carboxylic acid 5-chloromethyl-2-oxo-1,3-dioxol-4-ylmethyl ester.

The chemical structures of impurities OLM-Me, OLM-Cl, and OLM-eliminate are:

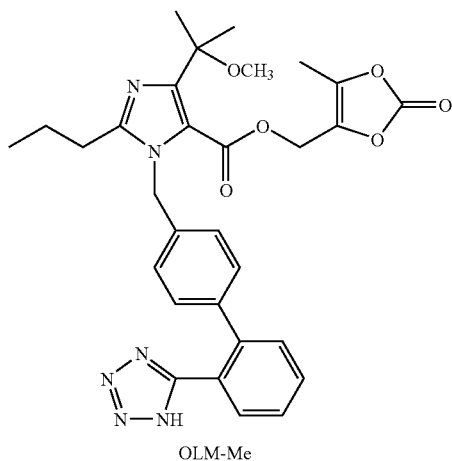

OLM-Me

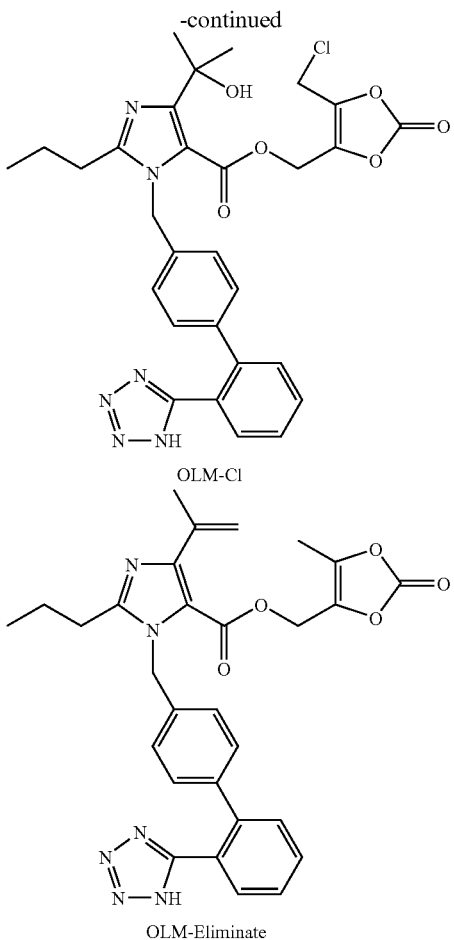

The precursors of impurities OLM-Me and OLM-eliminate can form during the Grignard reaction, reaction step D in the synthesis route described previously. The formation of the precursors of impurities OLM-Me and OLM-eliminate is illustrated as follows:

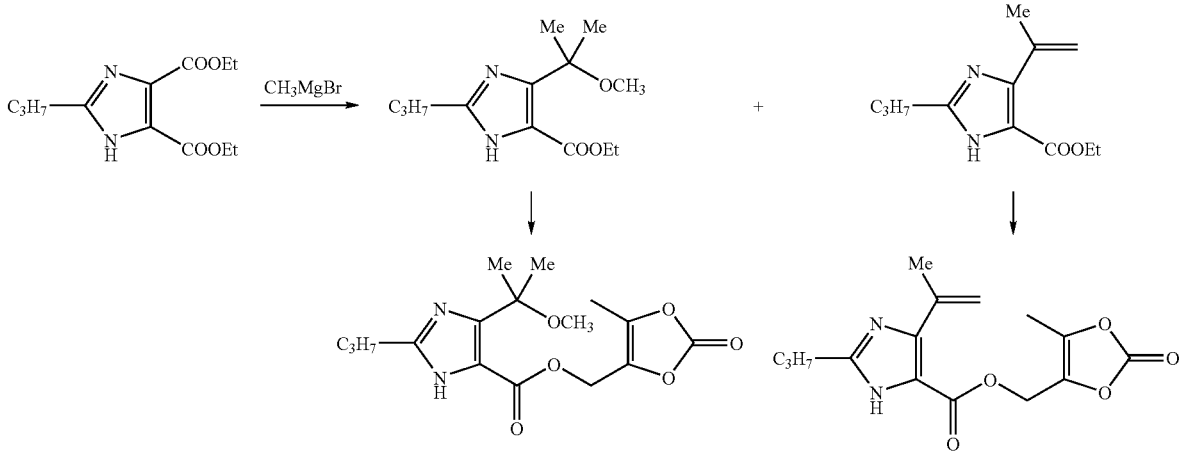

The precursor of impurity OLM-Cl can form during reaction step K when the coupling reagent chloro-medoxomil(4-chloromethyl-2-oxo-1,3-dioxolene) contains some dichloromedoxomil(4,5-dichloro-dimethyl-2-oxo-1,3-dioxolene):

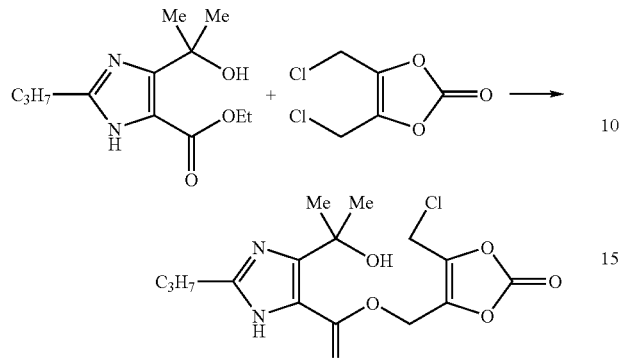

The impurities OLM-Me, OLM-Cl, and OLM-eliminate have no known medicinal effect. The impurities at the trityl olmesartan medoxomil (MTT) stage—MTT-Me, MTT-Cl, and MTT eliminate—are not used for synthesizing olmesartan medoxomil. Structures for MTT-Me, MTT-Cl, and MTT are described below.

By selecting trityl olmesartan medoxomil with low levels of MTT-Me, MTT-CL, and MTT eliminate, one can use the selected MTT to synthesize olmesartan medoxomil with low levels of impurities OLM-Me, OLM-Cl, and OLM-eliminate.

In one embodiment, the present invention provides a process for preparing olmesartan medoxomil containing less than about 0.1% area by HPLC of one or more of the following impurities: OLM-Me, OLM-CL, and OLM-eliminate. This process includes the steps of: obtaining a sample of trityl olmesartan medoxomil (MTT); measuring the amount of one or more impurities selected from the group consisting of MTT-Me, MTT-Cl, and MTT-eliminate in the sample of trityl olmesartan medoxomil; selecting a sample of trityl olmesartan medoxomil in which the amount of one or more of the measured impurities is less than about 0.1%; and synthesizing olmesartan medoxomil from the selected trityl olmesartan medoxomil sample. Preferably, the amount of each of the three impurities in the starting material and/or the final product is less than about 0.1%. More preferably, the combined amount of the three impurities is less than about 0.1%.

The chemical structures of MTT-Me, MTT-Cl, and MTT-eliminate are:

MTT-Me

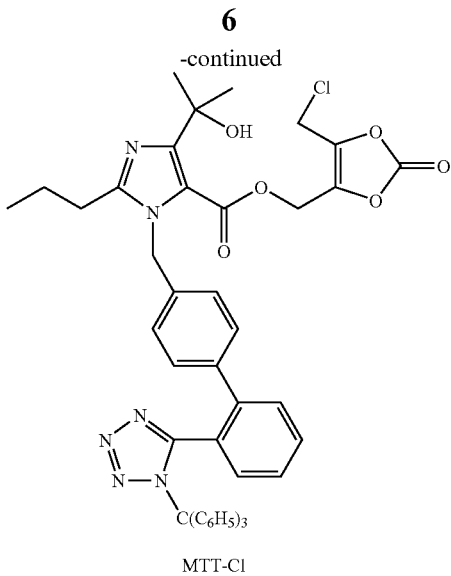

MTT-Cl

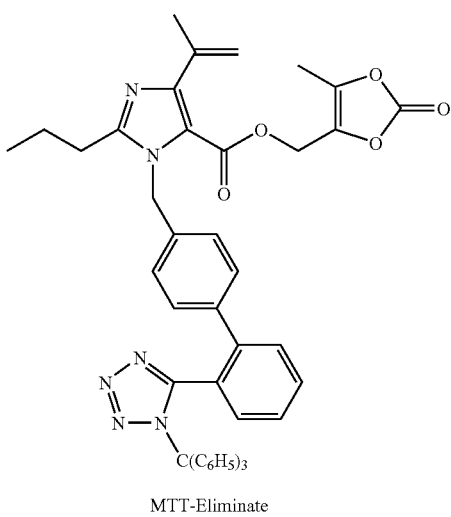

MTT-Eliminate

The amounts of MTT-Me, MTT-Cl, and MTT-eliminate are measured using HPLC. The amounts of OLM-Me, OLM-Cl and OLM-eliminate are also measured using HPLC. An exemplary impurity profile determination is described in Example 1.

One can use any method known in the art to synthesize olmesartan medoxomil from trityl olmesartan medoxomil, such as the process described in U.S. Pat. No. 5,616,599. Olmesartan medoxomil can be synthesized from trityl olmesartan medoxomil by a method including the steps of: contacting trityl olmesartan medoxomil with an acid in a water miscible organic solvent, with or without water, to obtain a solution of olmesartan medoxomil and a precipitate of triphenyl carbinol; separating the precipitate of triphenyl carbinol from the solution of olmesartan medoxomil; and contacting the solution of olmesartan medoxomil with a base to obtain a precipitate of olmesartan medoxomil. Preferably, trityl olmesartan medoxomil is contacted with the acid in a water miscible organic solvent and water. Most preferably, a mixture of acetone and water is used.

EXAMPLES

Impurity Profile Determination of MTT (Raw Material of Olmesartan Medoxomil)

| HPLC | |
|---|---|
| Column & packing | Discovery HS C18 50 * 4.6 mm, 3μ C.N 269250-U |
| Eluent A: | 0.025M NaClO$_4$ adjusted to pH = 2.5 with HClO$_4$ |
| Eluent B: | Acetonitrile |

| Gradient of Eluent: | Time (min) | Eluent A (%) | Eluent B (%) |
|---|---|---|---|
| | 0 | 70 | 30 |
| | 10 | 60 | 40 |
| | 20 | 40 | 60 |
| | 35 | 40 | 60 |

| | |
|---|---|
| Stop time: | 35 min |
| Equilibration time: | 5 min |
| Flow: | 1.5 ml/mm |
| Detector: | 220 nm |
| Injection volume: | 10 μl |
| Diluent | Acetonitrile |
| Column temperature | 25° C. |
| Autosampler temperature | 5° C. |

Sample Solution Preparation

Weigh accurately about 15 mg of MTT sample into a 50 ml volumetric flask, dissolve, and dilute to volume with diluent.

Method

Inject sample solutions continuing the chromatogram up to the end of gradient.

Determine the area of each impurity using suitable integrator.

Calculations

Any impurity in a sample is calculated as follows:

$$\% \text{ Impurity in sample} = \frac{\text{area impurity in sample}}{\sum \text{Areas of all peaks}} \times 100$$

RRT of the Substances

| Substance | RT | RRT |
|---|---|---|
| TPC | 16.28 | 0.70 |
| MTT | 23.20 | 1.00 |
| MTT-Methyl | 24.70 | 1.06 |
| MTT-Cl | 24.96 | 1.08 |
| MTT-Eliminate | 25.33 | 1.09 |

The detection limit in the HPLC method is 0.01%.

Example 1

Preparation of Crude Olmesartan Medoxomil

A 250 round bottom flask was loaded with MTT (10 g), acetone/water (2/2 vol.), and 3 eq of H$_2$SO$_4$. The mixture was stirred at 40° C., and after 2-4 hrs, triphenyl carbinol (TPC) was precipitated by the addition of water and filtrated out. NaHCO$_3$ was added to the filtrate and the mixture was cooled to room temperature and stirred for 1 hr. Crude olmesartan medoxomil was obtained as white crystals (90% yield).

Example 2

Preparation of Olmesartan Medoxomil Crystals

A 1 L flask was charged with acetone (4% water). Crude olmesartan medoxomil (10 g) was added, and the mixture was heated to reflux (1 hr). After cooling to room temperature, water (10 vol) was added. The mixture was stirred (1 hr). Then the precipitate was filtered and dried at 45° C. under 10 mm Hg (yield 90%).

Having thus described the invention with reference to particular preferred embodiments and illustrative examples, those in the art can appreciate modifications to the invention as described and illustrated that do not depart from the spirit and scope of the invention as disclosed in the specification. The examples are set forth to aid in understanding the invention but are not intended to, and should not be construed to, limit its scope in any way. The examples do not include detailed descriptions of conventional methods.

What is claimed is:

1. A process for preparing olmesartan medoxomil containing less than about 0.1% of one or more of

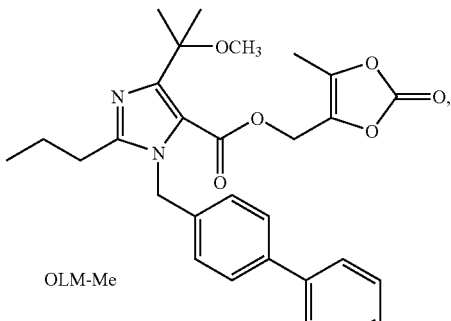

OLM-Me

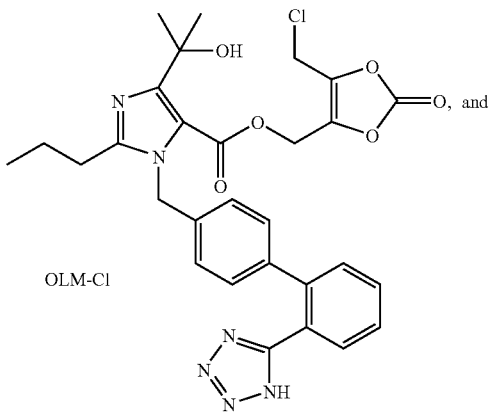

OLM-Cl

-continued

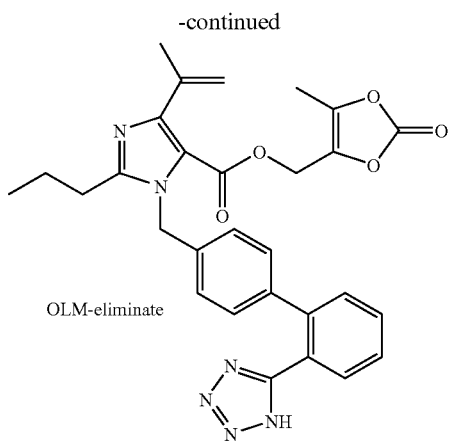

OLM-eliminate comprising:
 a) obtaining a sample of trityl olmesartan medoxomil;
 b) measuring the amount of one or more impurities selected from the group consisting of

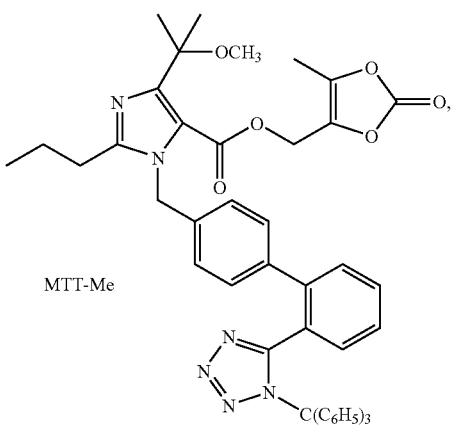

MTT-Me

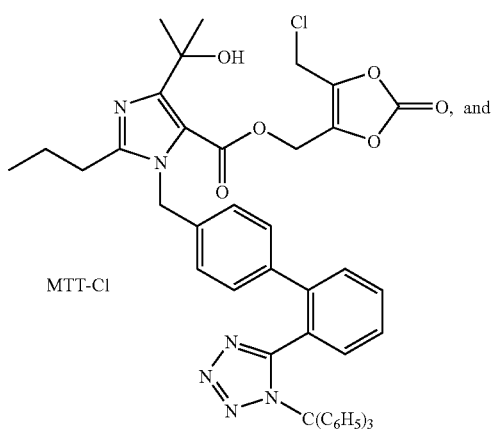

MTT-Cl

-continued

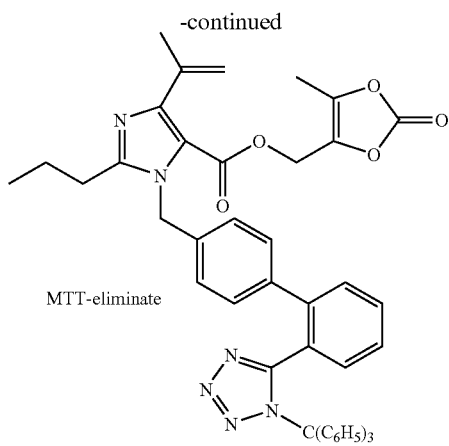

MTT-eliminate in the sample of trityl olmesartan medoxomil;
 c) selecting a sample of trityl olmesartan medoxomil in which the amount of one or more of the measured impurities is less than about 0.1%;
 d) combining the trityl olmesartan medoxomil from step c) with an acid in a solvent to produce triphenyl carbinol;
 e) preparing a filtrate comprising olmesartan medoxomil by precipitating and filtering out the triphenyl carbinol;
 f) adding a base to the filtrate; and
 g) cooling the filtrate of step f) to obtain olmesartan medoxomil.

2. The process of claim 1, wherein the amount of each of the impurities

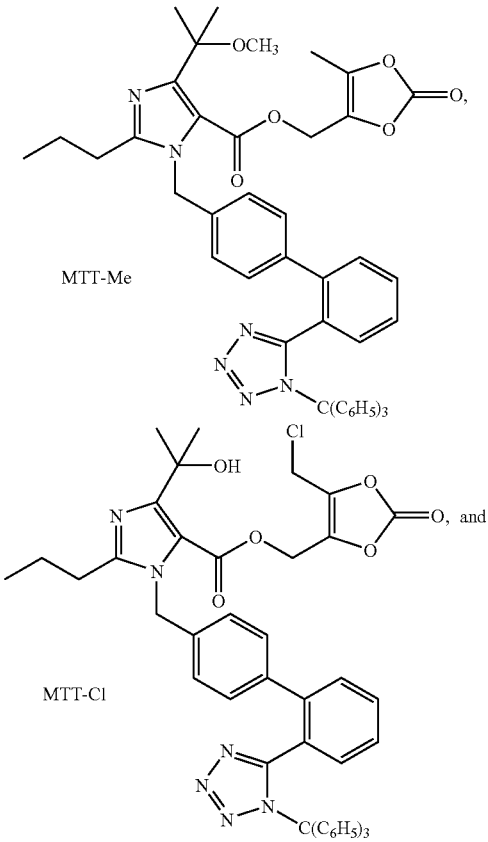

MTT-Me

MTT-Cl

-continued

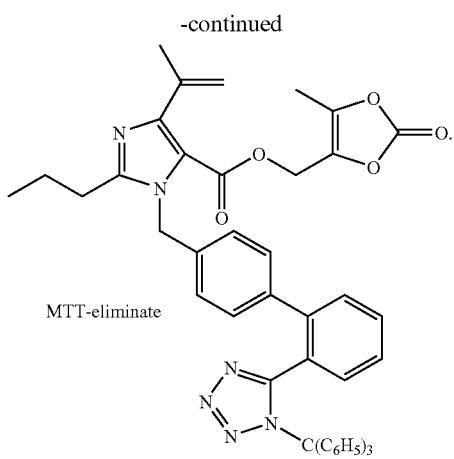

MTT-eliminate in the selected sample of step c) is less than about 0.1%.

3. The process of claim 1, wherein the combined amount of the impurities

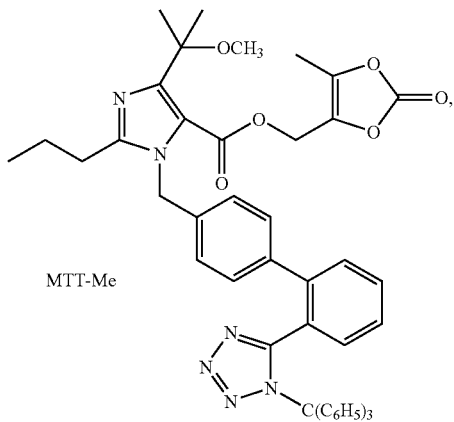

MTT-Me

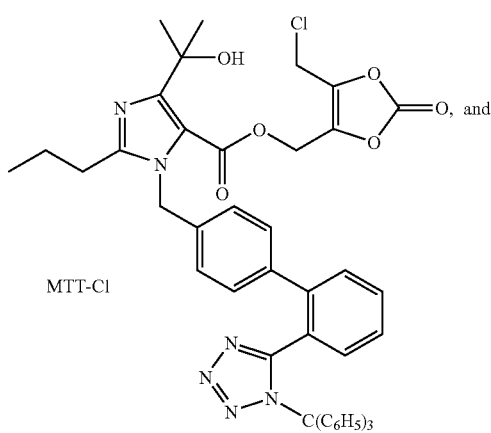

MTT-Cl

-continued

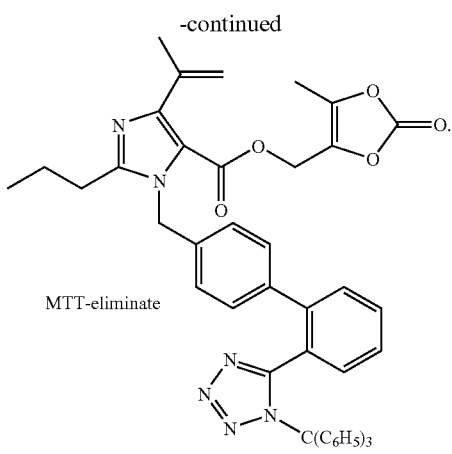

MTT-eliminate in the selected sample of step c) is less than about 0.1%.

4. The process of claim 1, wherein the one or more impurities in step b) is measured by HPLC.

5. The process of claim 1, wherein the amount of each of the impurities

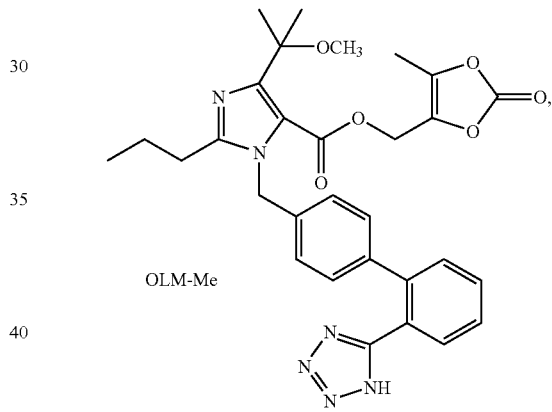

OLM-Me

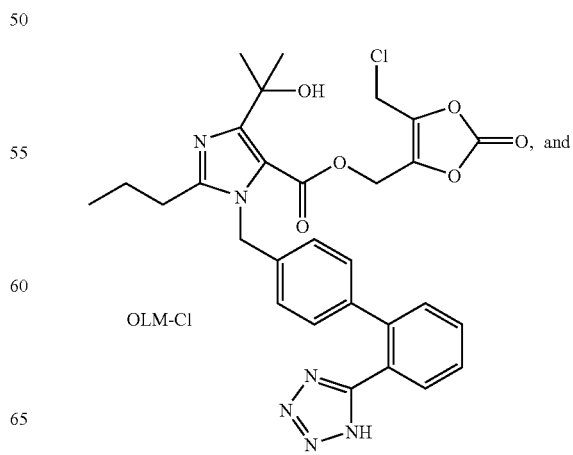

OLM-Cl

-continued

OLM-eliminate in the olmesartan medoxomil synthesized in step g) is less than about 0.1%.

6. The process of claim 5, wherein the combined amount of the impurities OLM-Me OLM-Cl -continued OLM-eliminate in the olmesartan medoxomil synthesized in step g) is less than about 0.1%.

7. The process of claim 5, wherein the impurities

OLM-Me

OLM-Cl, and

-continued

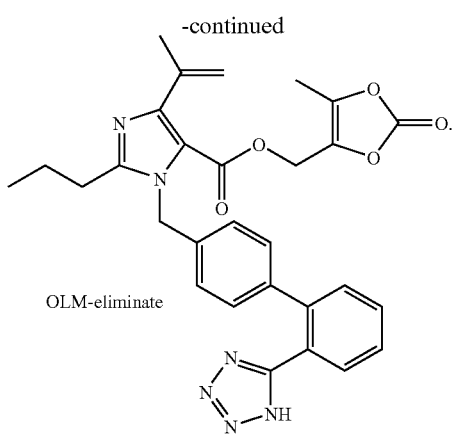

OLM-eliminate in the olmesartan medoxomil synthesized in step g) are measured by HPLC.

8. The process of claim 1, wherein the solvent comprises a water miscible organic solvent and water.

9. The process of claim 8, wherein the water miscible organic solvent is acetone.

10. The process of claim 1, wherein the acid is $H_2SO_4$.

11. The process of claim 1, wherein step d) further comprises heating at 40° C. for 2-4 hours.

12. The process of claim 1, wherein precipitating the triphenyl carbinol is carried out by addition of water.

13. The process of claim 1, wherein the base is $NaHCO_3$.

14. The process of claim 1, wherein step g) cooling comprises cooling the filtrate to room temperature with stirring for 1 hr.

* * * * *